(12) United States Patent
Cremer

(10) Patent No.: US 6,270,798 B2
(45) Date of Patent: *Aug. 7, 2001

(54) LOZENGE FOR THE MODIFIED RELEASING OF ACTIVE SUBSTANCES IN THE GASTROINTESTINAL TRACT

(75) Inventor: Karsten Cremer, Bonn (DE)

(73) Assignee: LTS Lohmann Therapie-Systeme AG (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/308,429

(22) PCT Filed: Nov. 17, 1997

(86) PCT No.: PCT/EP97/06395

§ 371 Date: Jul. 6, 1999

§ 102(e) Date: Jul. 6, 1999

(87) PCT Pub. No.: WO98/23262

PCT Pub. Date: Jun. 4, 1998

(30) Foreign Application Priority Data

Nov. 23, 1996 (DE) .............................................. 196 48 576

(51) Int. Cl.$^7$ ................................ A61K 9/20; A61K 9/00
(52) U.S. Cl. ........................... 424/464; 424/400; 424/470
(58) Field of Search ..................................... 424/400, 464, 424/470

(56) References Cited

FOREIGN PATENT DOCUMENTS

| 0 212 745 A2 | 8/1986 | (EP) . |
| 0 212 745 A2 * | 4/1987 | (EP) . |
| 0 601 508 A2 | 12/1993 | (EP) . |
| 2 565 107 A1 | 5/1984 | (FR) . |
| WO 91/19486 | 12/1991 | (WO) . |

* cited by examiner

Primary Examiner—Jose'G Dees
Assistant Examiner—Konata M George
(74) Attorney, Agent, or Firm—D. Peter Hochberg; Katherine R. Vieyra; William H. Holt

(57) ABSTRACT

A pharmaceutical lozenge for the modified release of active compounds in the gastrointestinal tract is described, with active-compound-containing particles which have a first coating controlling the release and a further, outer coating with saliva-resistant properties. The first coating, which controls the release of active compound, can have release-delaying or enteric properties.

9 Claims, No Drawings

LOZENGE FOR THE MODIFIED RELEASING OF ACTIVE SUBSTANCES IN THE GASTROINTESTINAL TRACT

BACKGROUND OF THE INVENTION

1. Field of the Invention

The invention relates to a pharmaceutical lozenge for the modified release of active compounds in the gastrointestinal tract, with active-compound-containing particles which have a first coating controlling the release and a further, outer coating with saliva-resistant properties.

2. Description of the Prior Art

Orally administrable presentation forms having modified active compound release can serve various therapeutic aims. The most frequent aims are the protection of the gastric mucosa from a harmful active compound or the protection of the active compound from the acidic medium in the stomach on the one hand, which is brought about by enteric coatings; moreover the control of the release rate over a relatively long time, which can be achieved by various release-delaying measures and leads to plasma levels with relatively low variations, a better tolerability as a result and a longer efficacy of the administration.

A formulation with modified active-compound release cannot be equally easily developed in the case of all pharmacologically suitable active substances. As a rule, it necessitates a number of additives with the aid of which the desired effects can be achieved. These additives correspondingly clearly increase the mass of the presentation form. In presentation forms with prolonged release of active compound, the dose to be administered is additionally increased compared to a simple presentation form. In the case of various active compounds, on account of their dose, no presentation forms having prolonged release of active compound could be developed using the possibilities known until now, since they could not be swallowed in the form of a capsule or tablet because of the resulting dimensions. Thus various antibiotics, for example, must still be orally administered three to four times daily although it is known that in the case of administration more than twice daily the reliability of taking by patients is low. In the case of antibiotics, the non-delayed-release single dose is frequently already 500 to 1000 mg, which together with the auxiliaries necessary for pharmaceutical formulation leads to capsules or tablets which can only be swallowed with difficulty. A delayed-release preparation prepared on the basis of conventional techniques with more than 1000 mg of active compound and an increased content of auxiliaries can virtually no longer be swallowed.

The provision of a presentation form which is easy and pleasant to take with modified release of active compound, which is also suitable for active compounds which have to be taken in high single doses, is desirable.

According to the invention, the problem of the taking of high doses should first of all be solved by administering a multiparticulate active compound preparation which is compressed to give a lozenge, whose particles are individually coated to achieve a modified release. The coated particles are released in finely divided form on sucking the tablet in the mouth and can be easily swallowed with the saliva.

The presentation form of the lozenge has been known for a long time and is frequently used in order to deliver active compounds to the diseased oral and pharyngeal mucosa. The lozenge can also be suitable for systemically active substances if the substances have a pleasant taste and are to be absorbed without delay. For the solution of the problem, the presentation form of the lozenge is employed, since it is able to accommodate more active-compound and auxiliary mass without loss of its administrability than a tablet intended for swallowing. Lozenges having a mass of more than 4 g are on the market and are apparently accepted by patients without problem.

In principle, the prior art allows the compression of coated particles having modified release of active compound, although the intended use according to the invention with its advantages—administration as a lozenge with suitability even for high doses of active compound—was neither recognized nor described as a solution of the problem presented above.

Thus the Patent Applications EP 153 104 and EP 355 247 teach, for example, the compression of release-delaying coated particles containing active compound to give tablets, a process which is also described in other sources. Moreover, the Patent Specification U.S. Pat. No. 5,464,632 discloses a rapidly disintegrating tablet intended for sucking or for disintegration in the mouth, which contains the active compound optionally in the form of coated particles for modified release. However, with this tablet in the case of disintegration in the mouth it is to be expected that portions of the active compound have already been released through the coating of the particles into the oral cavity and in the course of this leaves behind an adverse taste impression.

Analogously, the presentation form of the lozenge, as is claimed in the present invention, does also solve, on the one hand, the problem of the administrability of relatively large amounts of active compound and auxiliaries, but on the other hand creates new problems. For one thing, in the case of enteric-coated particles the coatings are exposed to the pH-neutral saliva, as a result of which they prematurely disintegrate and can no longer achieve the desired protective effect in the stomach. For another thing, in the case of particles which are provided with release-delaying coatings, portions of the active compound have already been released in the oral cavity by diffusion, which is not acceptable, in particular in the case of unpleasantly tasting substances.

SUMMARY OF THE INVENTION

A need therefore exists for a further improved presentation form having modified release of active compound for administration of high doses of active compound, which does not have the disadvantages mentioned. This object, on which the invention is based, is achieved by a pharmaceutical-presentation form according to one of the two main claims: in addition to the special design as a lozenge, the tablet according to the invention overcomes the disadvantages of the prior art in that its active compound is present in the form of doubly or two-layer coated particles, a first, inner coating serving for the release of the modified active compound, while a further, external coating is saliva-resistant, but dissolves in the acidic medium of the stomach and thereby ensures that during the sucking of the tablet active compound is not released into the oral cavity. The first, inner coating of the particles can modify the release of active compound according to one of the two main claims either in that the release commences only after the gastric passage of the particle, or it can be designed as a membrane which is insoluble in the gastric and intestinal juice, but through which the active compound can slowly diffuse outwards and be released with a delay.

DESCRIPTION OF THE PREFERRED EMBODIMENTS

According to the invention, the active-compound-containing particles are pressed together with suitable auxiliaries to give lozenges which, owing to their composition, slowly erode in the mouth and in the course of this release the particles into the saliva. The saliva containing the coated particles is then swallowed. Self-experiments showed that particles of up to approximately 100–200 μm in diameter are perceived to be only moderately troublesome on swallowing.

Film-forming polymers which can be employed for the production of a saliva-resistant coating are known to the person skilled in the art. Frequently, a copolymer based on dimethylaminoethyl methacrylate and neutral methacrylic acid esters having the trade name Eudragit E (Röhm) is employed for this purpose. The basic character of the dimethylaminoethyl methacrylate provides for solubility in the acidic medium, such as, for example, in the gastric juice, while the solubility in the relatively neutral saliva is rather low. If the thickness of the film is suitable, a coating can therefore be produced using this copolymer which resists disintegration in the saliva for a longer time, but which dissolves rapidly in the stomach. Alternatively, all other film-forming polymers which have a markedly better solubility in the gastric juice than in the saliva can be used for this purpose.

Release-delaying film coatings are widespread in the technology of solid oral presentation forms. The polymers employed for this typically have a low solubility in aqueous media both at acidic and at neutral to basic pHs. With sufficient thickness and mechanical strength of the film coating, this dissolves neither in the saliva nor in the gastric or intestinal juice. On the other hand, the thickness must not be too great, since the film coating must allow the diffusion of water into the active compound reservoir, where the active compound is continuously dissolved and diffuses outwards through the coating in dissolved form. A large number of polymers have been employed for this purpose; examples which may be mentioned are: polymers from the group consisting of the cellulose esters, such as, for example, cellulose acetate, representatives of the cellulose ethers group, such as, for example, ethylcellulose, certain poly(meth)acrylic acid derivatives, e.g. Eudragit RL or RS (Röhm) and certain polyvinyl derivatives such as polyvinyl acetate.

The polymers typically used for the preparation of film coatings which are resistant to gastric juice but soluble in small intestinal juice have an extremely low solubility in the acidic medium with markedly better solubility in the neutral pH range. These properties are seen especially in those polymers which contain acidic groups which are present in undissociated form in the gastric juice. Examples which may be mentioned are: hemiesters of divalent acids such as succinic or phthalic acid with cellulose ethers, cellulose esters, polyvinyl derivatives, carboxymethylcelluloses or poly(meth)acrylic acids, such as are contained in Eudragit L or S (Röhm).

Elasticity and strength of the film coatings of the particles are a prerequisite for the functionality of the pharmaceutical form, since the coatings must not be damaged by the strong mechanical stress during compression or tabletting; at least the predominant majority of the particles contained in the lozenge should have two intact coating layers within the meaning of the invention. It is known to the person skilled in the art that the elasticity, flexibility and strength of the polymer films is dependent on the polymer type, molecular weight, degree of substitution of the film-forming agents employed, but also on the nature and amount of the additives employed. In particular, plasticizers or additives employed for other purposes, but which have a plasticizing action, have a considerable effect on the mechanical film properties. For most of the polymers which can be employed within the meaning of the invention, the prior art knows suitable plasticizers for the production of certain mechanical properties; the person skilled in the art is able by means of suitable experiments to determine the optimum amount of plasticizer for the purpose of the tabletting according to the invention of coated particles, which can differ completely from the amount recommended for other purposes.

Two examples should serve to illustrate possible embodiments of the invention which, however, only have illustrative character; the person skilled in the art is able to develop further examples using different recipes and preparation processes.

EXAMPLE 1

Lozenges of Enteric-coated Ibuprofen Particles Comprising 600 mg of Ibuprofen

Ibuprofen micropellets are first prepared by granulating, extruding and spheronizing. For this, 700 g of ibuprofen, 180 g of microcrystalline cellulose and 120 g of lactose monohydrate are mixed in a powder blender and then made into a paste in a suitable kneader mixer with addition of n g of water to give a mass having a kneadable consistency. The mass is extruded through a specially made perforated disc having a hole diameter of 300 μm using an extruder, e.g. a single-screw extruder of the E 40/10 D type (Gabier), cut and, if possible, rounded in the on-line process, e.g. in a spheronizer of the type (Gabler) R 250. The micropellets are then dried in a dryer to a residual moisture of about 2–3%, which can be carried out in a suitable fluidized bed apparatus, but preferably in the apparatus intended for the coating of the pellets, e.g. the fluidized bed granulator/dryer/coater of the Uni-Glatt type (Glatt).

For the production of the first, enteric-coating, the pellets are sprayed into the fluidized bed via a two-substance nozzle at about 1–2 bar in the top-spray arrangement and at a spray velocity of 10 ml/min with a dispersion of 95 g of Eudragit® L30 D-55, 45 g of Eudragit® NE 30 D (both Röhm), 8 g of triethyl citrate, 12 g of polyethylene glycol 6000, 20 g of talc and 90 g of water up to a dry weight increase of 12%. A suitable spray temperature is 38–43° C., and subsequent drying at 30–35° C. should take place.

The enteric-coated particles prepared in this way are then provided according to the invention with a second, saliva-resistant coating. Alternatively, the production of the saliva resistance can also be carried out without transition by means of a change in the spray medium in the preceding process. A suitable spray solution for this is composed of 240 g of Eudragit® E 12.5, 18 g of polyethylene glycol 6000, 12 g of microcrystalline cellulose, 12 g of magnesium stearate and 220 g of acetone. It can be sprayed into the apparatus described above at the same pressure and the same spray velocity, but preferably at a temperature reduced to about 30° C. The spray process is complete with a weight increase in the pellets of 11%.

After the subsequent drying, the particles now provided with two coatings are compressed to give lozenges. For this, 1066 g of pellets—these contain 600 g of ibuprofen—are mixed in a powder blender with 260 g of sorbitol (a directly tablettable quality is necessary), 2 g of colloidal silica, 28 g of stearic acid and 11 g of magnesium stearate and pressed in a tablet press to give tablets weighing 1367 mg, e.g. with a diameter of 18 mm.

EXAMPLE 2

Lozenges of Release-delaying Coated Ibuprofen Particles Comprising 600 mg of Ibuprofen The preparation is carried out analogously to Example 1 with the assumption that a dispersion of 110 g of Eudragit RS 30 D, 25 g of talc, 28 g of triethyl citrate and 15 g of polyethylene glycol 6000 is used for the production of the release-modifying coating.

These working examples illustrate the principle of the invention; depending on prioritization of the product properties, e.g. low particle sizes for the sensory improvement of the sucking or disintegration properties of the tablet or lower auxiliary contents for the reduction of the production costs, they can be markedly optimized in the direction of one of the target parameters.

The invention has been described in detail with particular emphasis on the preferred embodiments, but variations and modifications within the spirit and scope of the invention may occur to those skilled in the art to which the invention pertains.

What is claimed is:

1. Pharmaceutical lozenge pressed from pulverulent or granular press material wherein the press material contains an active-compound preparation in the form of at least two-layer coated particles in addition to customary auxiliaries suitable for the production of lozenges, an outer coating layer being saliva-resistant, but soluble in gastric juice, and an inner coating layer being largely disintegration resistant in aqueous media, but allowing a delayed release of active compound by diffusion, and wherein said lozenge erodes in the mouth upon oral administration, thus releasing said coated particles in finely divided form into the saliva.

2. A pharmaceutical presentation form for the modified release of active compounds into the (gastrointestinal tract comprising individually coated particles of said active compound, wherein the coating of said particles comprises a first inner coating layer which is capable to modify the release of said active compound in the gastrointestinal tract, and a second external coating layer which is resistant to saliva and soluble in the acidic medium of the stomach, said coated particles being released from said pharmaceutical presentation form upon sucking in the mouth, thereby being able to be swallowed with the saliva in finely divided form.

3. A pharmaceutical presentation form according to claim 2 wherein said first inner coating layer is resistant to gastric juice and soluble in the small intestine.

4. A pharmaceutical presentation form according to claim 2 wherein said second external coating layer comprises as a film-forming polymer one or more polymers selected from the group consisting of dimethylaminoethyl methacrylates and methyacrylic acid esters.

5. A pharmaceutical presentation form according to claim 2 wherein said second external coating layer comprises as a film-forming polymer one or more polymers selected from the group consisting of cellulose ethers cellulose esters polyacrylic acid derivatives, polymethacrylic acid derivatives, and polyvinyl derivatives.

6. A pharmaceutical presentation form according to claim 3 wherein said first inner coating layer comprises as a film-forming polymer one or more polymers selected from the group consisting of cellulose ethers, cellulose esters, polyvinyl acetate phthalates, succinates carboxymethylcelluloses, polyacrylic acid derivatives, and polymethacrylic acid derivatives.

7. A pharmaceutical presentation form according to claim 2 wherein said pharmaceutical presentation form is a tablet or lozenge.

8. A process for the preparation of a pharmaceutical presentation form for the modified release of active compounds into the gastrointestinal trace comprising the steps:

a) preparation of particles of said active compound, b) coating the particles of step a) into a spray application process with a first coating material that is capable to modify the release of said active Compound in the gastrointestinal tract, c) coating the particles of step b) in a spray application process with a second coating material that is resistant to saliva and soluble in the acidic medium of the stomach, and d) compressing the particles of step c) with auxiliary substances in a tablet machine.

9. A process for the preparation of pharmaceutical presentation form according to claim 8, wherein the step of preparation of particles further includes the preparation of auxilliary substances.

* * * * *